United States Patent [19]

Leuchter et al.

[11] Patent Number: 5,230,346
[45] Date of Patent: Jul. 27, 1993

[54] DIAGNOSING BRAIN CONDITIONS BY QUANTITATIVE ELECTROENCEPHALOGRAPHY

[75] Inventors: Andrew F. Leuchter, Los Angeles; Ian A. Cook, Beverly Hills, both of Calif.

[73] Assignee: The Regents of the University of California, Oakland, Calif.

[21] Appl. No.: 830,676

[22] Filed: Feb. 4, 1992

[51] Int. Cl.$^5$ .............................................. A61B 5/04
[52] U.S. Cl. .................................................. 128/731
[58] Field of Search ........... 128/731, 732, 641, 419 R, 128/791

[56] References Cited

PUBLICATIONS

Mary J. De Leon, Ajax E. George,. Jeffrey D. Miller, et al., "Altered Patterns of Positron-Emission Tomography Glucose Metabolism in Alzheimer Patients with Microvascular White Matter Disease", in *American Journal of Physiologic Imaging* (vol. 3: 1988, pp. 52-53).
Andrew F. Leuchter, M.D. and Donald O. Walter, Ph.D., "Diagnosis and Assessment of Dementia using Functional Brain Imaging", *International Psychogeriatrics* (vol. 1: 1, 1989, pp. 63-72).
Sheldon E. Jordan, Ralph Nowacki, and Marc Neuer, "Computerized Electroencephlography in the Evaluation of Early Dementia", *Brain Topography* (vol. 1: 4, 1989, pp. 271-282).
Barry S. Oken, M.D., Keith H. Chiappa, M.D., and Martin Salinsky, M.D., "Computerized EEG Frequency Analysis: Sensitivity and Specificity in Patients with Focal Lesions", in *Neurology* (vol. 39: Oct. 1989, pp. 1281-1287).
Andrew Leuchter, M.D., James E. Spar, M.D., Donald Walter, M.D., et al., "Electroencephalographic Spectra and Coherence in the Diagnosis of Alzheimer's Type and Multi-infarct Dementia", in *Archives of General Psychiatry* (vol. 44: Nov. 1987, pp. 993-998).
J. Breslau, A. Starr, N. Sicotte, et al., "Topographic EEG changes with normal aging and SDAT", in *Electronencephalography and Clinical Neurophysiology* (vol. 72: 1989, pp. 281-289).
V. E. Pollack, L. S. Schneider and S. A. Lyness, "EEG amplitudes in healthy, Late-middle-aged and elderly adults: normality of the distributions and correlations with age", in *Electroencephalography and Clinical Neurophysiology* vol. 75: 1900, pp. 276-288).
Fernando Torres, Angelina Faoro, Ruth Loewenson et al., "The Electroencephalogram of Eldery Subjects Revisited", *Electroencephalography and Clinical Neurophysiology* (vol. 56: 1983, pp. 391-398).
M. Onofri, D. Gambi, G. Malatesta et al., "Electrophysiological Techniques in the Assessment of Aging Brain: Lacunar State and Differential Diagnosis", in *Neuroepidemology*, vol. 29: 1989, (Suppl. 2).
Hellmuth Lechner, Reinhold Schmidt, Bertha Goetz, "Long-Term Experience of a Trial in Multi-Infarct Dementia", in *Neuroepidemiology* (vol. 9: 1990, pp. 228-232).
Gastone G. Celesia, "EEG and Event-Related Potentials in Aging and Dementia", in *Journal of Clinical Neurophysiology* (vol. 3: 2, 1986, pp. 99-111).
Ch. Logar, W. Grabmair, G. Schneider et al., "EEG changes in senile dementia of Alzheimer-type", *Z. EEG-EMG* (German Research Journal( (vol. 18: 1987, pp. 214-216).
"Letters on Brain Mapping", in *Clinical EEG Electroencephalography*, (vol. 21: 2, 1990, pp. 7-10).

(List continued on next page.)

Primary Examiner—Max Hindenburg
Attorney, Agent, or Firm—Charles Berman

[57] ABSTRACT

Determining the brain condition of a human between normal and abnormal as determined by dementia, and selectively between dementia of the Alzheimer's-type and multi-infarct dementia is effected. Measures of electrical output, spectral ratio and coherence value of the brain are determined. Selected scores are applied to the electrical output, spectral ratio and coherence values. A relationship between the scores and addi-tionally the scored value of a coherence ratio are effected to obtain a diagnostic evaluation.

44 Claims, 12 Drawing Sheets

OTHER PUBLICATIONS

David Loring, Daniel E. Sheer and John W. Largen, "Forty Hertz EEG Activity in Dementia of the Alzheimer Type and Multi-Infarct Dementia", in *Psychophysiology* (vol. 22: 1, pp. 116-121) 1985.

T. Erkinjuntti, T. Larsen, R. Sulkava et al., "EEG in the differential diagnosis between Alzheimer's disease and vascular dementia", in *Acta Neurological Scandananvia* (vol. 77: 1988, pp. 36≧43).

Richard P. Brenner, Richard F. Ulrich, Duane G. Spiker et al., "Computerized EEG Spectral Analysis in Elderly Normal, Demented and Depressed Subjects", in *Electroencephalography and Clinical Neurophysiology* (vol. 64: 1986, pp. 483-492).

K. P. O'Connor, J. C. Shaw and C. O. Ongley, "The EEG and Differential Diagnosis in Psychogeriatrics", in *British Journal of Psychiatry* (vol. 135: 1979, pp. 156-162).

Lawrence A. Coben, Warren Danziger and Martha Storandt, "A Longitudinal EEG Study of Mild Senile Dementia of Alzheimer Type Changes as 1 Year and at 2.5 Years", *Electroencephalography and Clinical Neurophysiology* (vol. 61: 1985, pp. 101-112).

Lawrence A. Coben, Warren L. Danziger, and Leonard Berg, "Frequency Analysis of the Resting Awake EEG in Mild Senile Dementia of Alzheimer Type", in *Electroencephalography and Clinical Neurophysiology* vol. 55: 1983, pp. 372-380).

R. W. Thatcher et al., "Cortico-Cortical Associations and EEG Coherence: A Two-Compartmental Model", *Electroencephalography and clinical Neurophysiology*, 64:123-143 (1986).

G. Fein et al., "Common Reference Coherence Data are Confounded by Power and Phase Effects", *Electroencephalography and clinical Neurophysiology*, 69:581-584 (1988).

C. C. French and J. G. Beaumont, "A Critical Review of EEG Coherence Studies of Hemisphere Function", *International Journal of Phychophysiology*, 1:241-254 (1984).

DIAGNOSING BRAIN CONDITIONS BY QUANTITATIVE ELECTROENCEPHALOGRAPHY

Portions of the work leading to this application were developed under a grant of the National Institute of Mental Health (NIMH) under Grant No. MH 40705. The NIMH may have rights in this application.

BACKGROUND

Diagnosing disorders and afflictions in the human brain with non-invasive procedures is important medically and scientifically.

This invention relates to determining the nature of brain conditions using quantitative electrophysiology. In particular, the invention relates to analyzing electroencephalographic information in a manner to permit assessment of the nature of brain conditions. The invention is further directed to give a characterization of afflictions such as dementia, being selective for multi-infarct dementia or Alzheimer's disease.

Information which is obtainable from an EEG includes conventional EEG data representative of electrical activity in different brain regions. When these data are digitized and processed as in quantitative EEG ("qEEG"), it is possible to obtain topographical brain mapping of electrical activity in different brain regions. From a qEEG unit, it is also possible to obtain measurements of absolute power, relative power, and evoked potentials. Quantitative EEG techniques represent an advance over traditional EEG methods because they permit the detection of trends which are difficult or impossible to discern by direct visual inspection of the EEG voltage tracings.

A shortfall of all these EEG and qEEG data is often the inability to provide convincing information regarding brain physiologic differences between normal and abnormal conditions, and to distinguish between the nature of different abnormal conditions.

Prior investigations of quantitative electroencephalography (qEEG) have detected several parameters that are useful in distinguishing elderly subjects with dementia from control subjects. They also are useful in determining the likelihood that a degenerative brain disease, such as Alzheimer's disease (DAT) that affects primarily the cerebral cortex, or a disease prominently affecting subcortical white matter, such as multi-infarct dementia (MID), are contributing to cognitive losses in an individual case. Most of these parameters, however, are of limited usefulness for the diagnosis of dementia, accurately classifying a majority of subjects only when clear impairment is present, rendering the parameter's information merely confirmatory.

SUMMARY

By the present invention, there is provided a method and means of minimizing the disadvantages of EEGs and providing for enhanced techniques of quantitative EEG analysis. The invention provides for information about brain electrical function that can be associated with specific diseases and syndromes and thus can assist in determining the likelihood of certain brain diseases.

Parameters have been identified that are reliably associated with dementia or other organic mental syndromes and establish the likelihood that syndromes such as DAT or MID are present.

According to the invention, the assessment of brain conditions in a human between normal and abnormal, abnormal being varying degrees of organic impairment or brain dysfunction, comprises determining measures of electrical output of the brain regions, relationships between output in different frequency bands (spectral ratios), and coherence values of the brain regions. Scores are allocated to each of the electrical output, spectral ratios and selectively coherence measures. A relationship between the scores permits for assigning a likelihood of a diagnosis between normal and dementia. The relationship also permits for determining the likelihood of a diagnosis between dementia of the Alzheimer-type (DAT) and multi-infarct dementia (MID).

By the invention, several different qEEG parameters are integrated into a Quantitative Cerebral Neurophysiology Scale (QCNS). These parameters include the electric output as measured by absolute EEG power, spectral power ratios, and coherence between brain regions linked by major neuroanatomic tracts.

The QCNS is established by allocating scores from predetermined selected integers between 0 and 5 to conditions representative between normal and abnormal. A score of 0 denotes a normal value; a score of 5 is representative of marked abnormality consistent with abnormality; middle integers represent intermediate departures from a normal brain condition. The scores for each of the electrical output regions, spectral ratio regions, and coherence between brain regions are added to provide a measure of dementia and non-dementia subjects.

The coherence value between brain regions connected by dense narrow bands of long corticocortical fibers and, secondly, by broad complex networks of corticocortical and cortico-subcortical fibers are measured to determine the likelihood of DAT or MID syndrome existing.

The invention covers a method of assessing brain conditions, apparatus for providing such provisions, and the use of such methodology and apparatus to perform assessments and characterizations of the human brain.

The invention is now further described with reference to the accompanying drawings.

DRAWINGS

Figure 4:
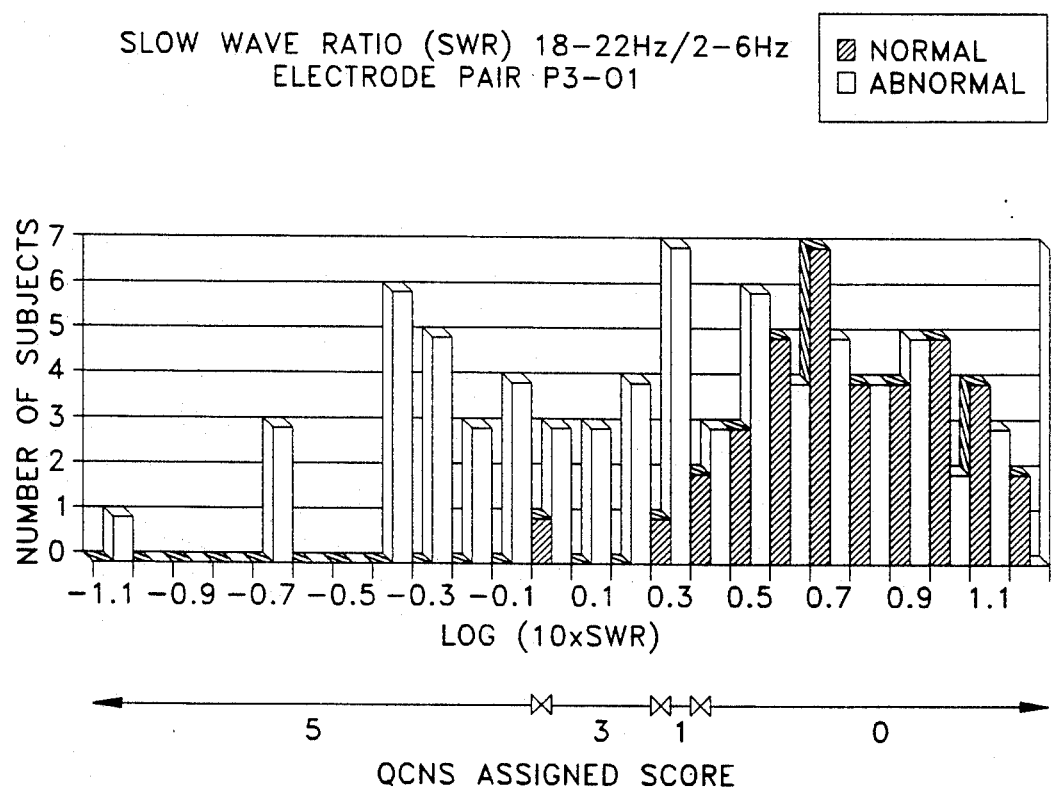

FIG. 4 is a histogram representation of a first set of slow wave ratios of the absolute power in the 18 to 22 Hz band relative to the value of absolute power in the low frequency band 2 to 6 Hz, namely, the ratio between a beta and a slow wave band from electrode pair P3-O1 near the back of the head, namely, the occiput. Data from normal control subjects and abnormal individuals with brain disorders are shown. The selected predetermined scores are illustrated between the values of 0, 1, 2, 3, and 5.

Figure 5:
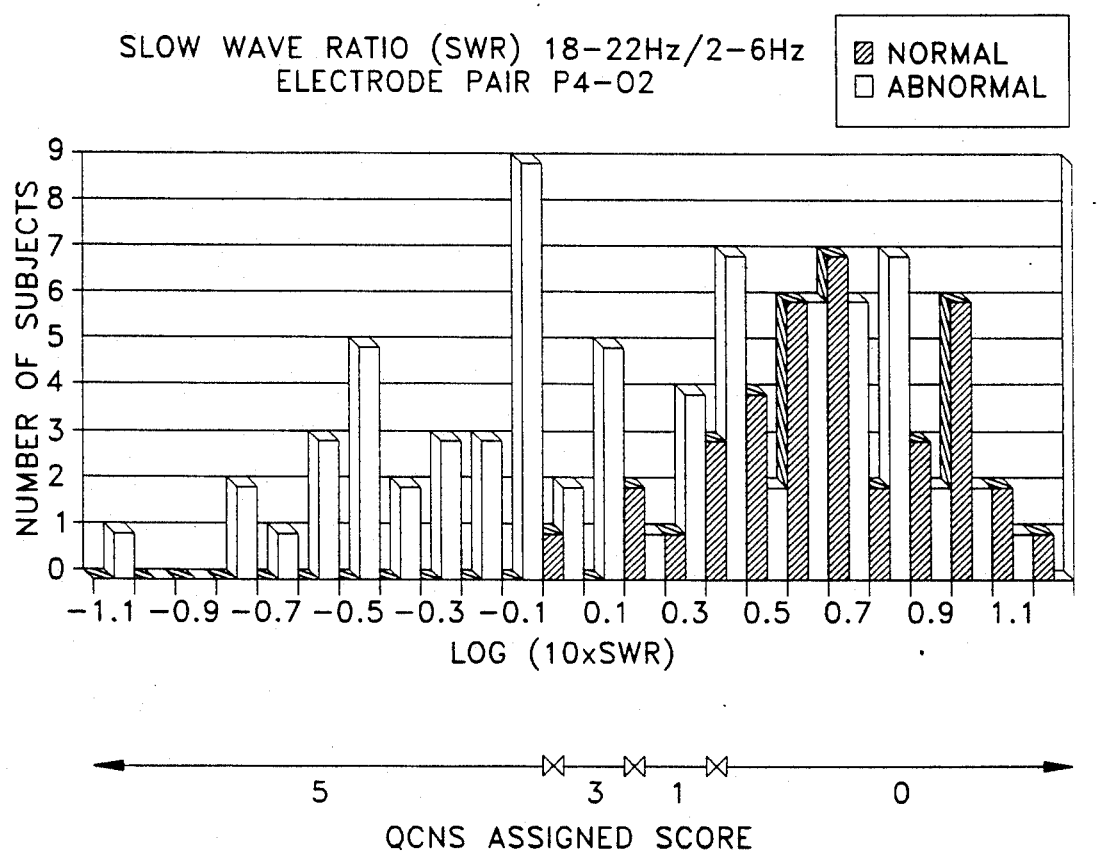

FIG. 5 is a histogram representation of a second set of slow wave ratios of the absolute power in the 18 to 22 Hz band relative to the value of absolute power in the low frequency band 2 to 6 Hz, namely, the ratio between the beta and delta bands from electrode pair P4-O2 near the back of the head, namely, the occiput. Data from normal control subjects and abnormal individuals with brain disorders are shown. The selected predetermined scores are illustrated between the values of 0, 1, 3, and 5.

Figure 6:
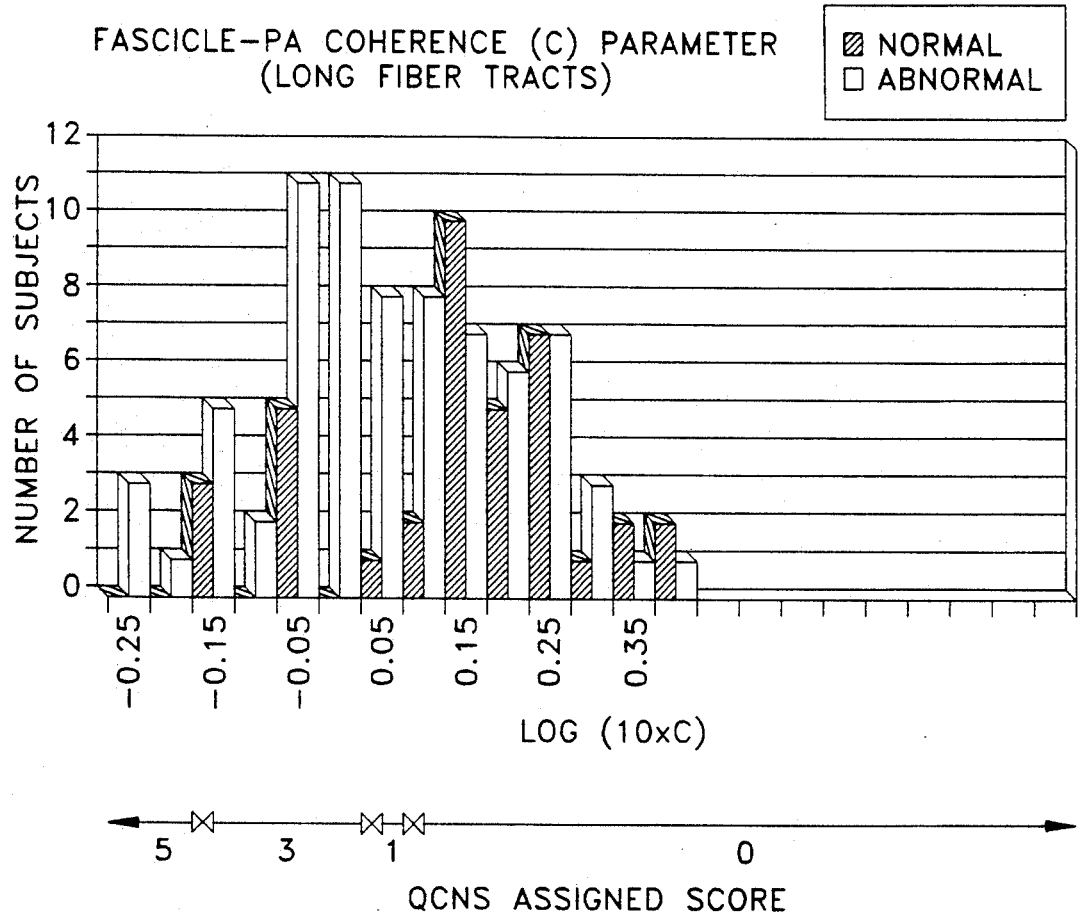

FIG. 6 is a histogram representation of namely, the coherence value between the posterior cortex and the brain regions in front of the head in the 14 to 18 Hz band hereinafter also called the FASCICLE-PA parameter. Data from normal control subjects and abnormal individuals with brain disorders are shown. The selected predetermined scores are illustrated between the values of 0, 1, 3, and 5.

Figure 7:
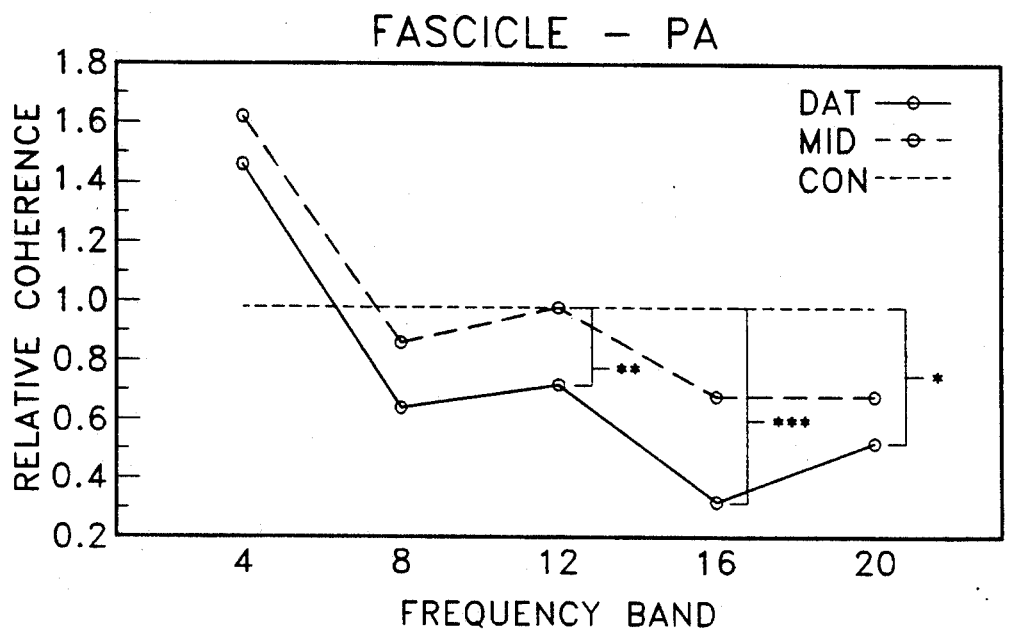

FIG. 7 is a graphical representation of the coherence values for the posterior cortex and the front of the head for all frequency bands. The coherence illustrates the difference between a DAT and a MID group as a proportion of the mean value for the normal elderly controls (CON) in the FASCICLE-PA parameter. Coherence is displayed for the DAT (○) and MID (□) groups as a proportion of the mean value for the CON group. Mean value for the CON group is standardized to 1.0 in each frequency band, and indicated by the dotted line across the middle of the figure. Frequency bands are displayed across the bottom of the figure, with numbers representing the center frequency of each band (i.e., "4" represents the 2-6 Hz band, "8" represents the 6-10 Hz band, etc.).

Figure 8:
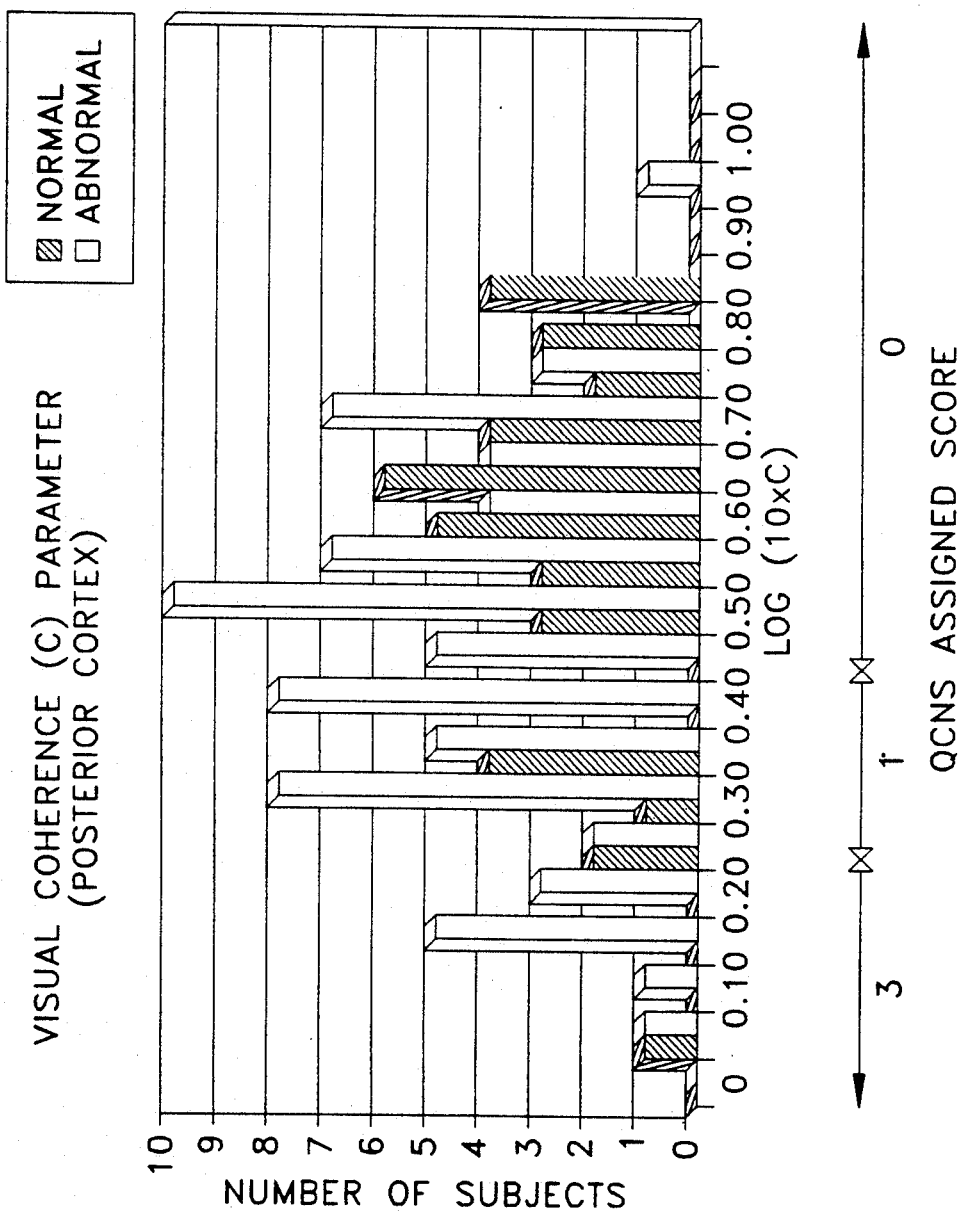

\*— difference between DAT and CON, $p<0.05$
\*\*— difference between DAT and CON, $p<0.01$
\*\*\*— difference between DAT and CON, $p<0.005$ FIG. 8 is a histogram representation of namely, the coherence value within the posterior cortex in the 6 to 10 Hz band displaying the difference between normal and abnormal groups hereinafter called the VISUAL parameter. The selected predetermined scores are illustrated between the values of 0, 1 and 3.

Figure 9:
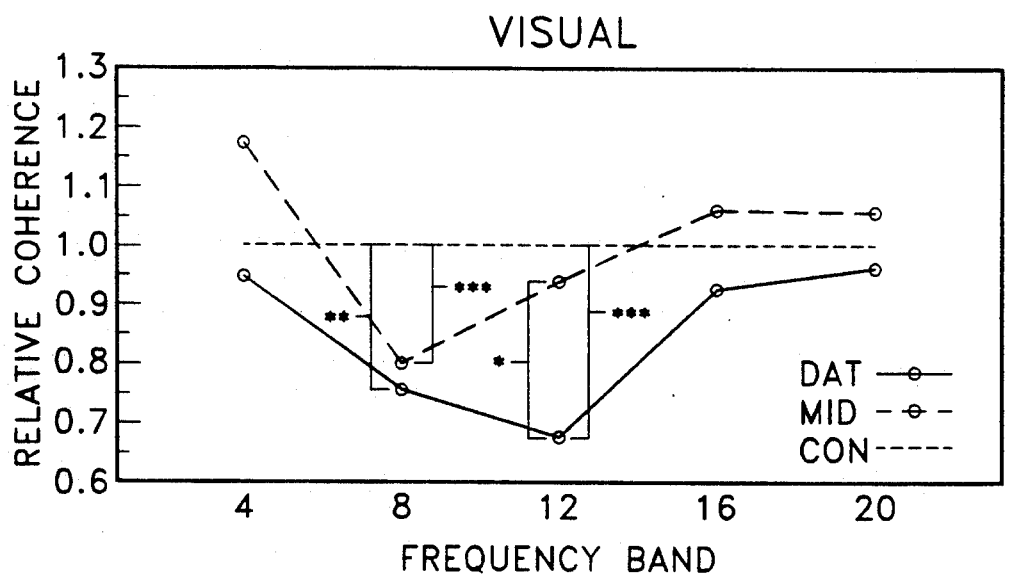

FIG. 9 is a graphical representation of the coherence values for the VISUAL measure for all frequency bands displaying the difference between DAT, MID and CON groups. Coherence is displayed for the DAT (○) and MID (□) groups as a proportion or the mean value for the CON group. Mean value for the CON group is standardized to 1.0 in each frequency band, and indicated by the dotted line across the middle of the figure. Frequency bands are displayed across the bottom of the figure, with numbers representing the center frequency of each band (i.e. "4" represents the 2-6 Hz band, "8" represents the 6-10 Hz band, etc.)

Figure 10:
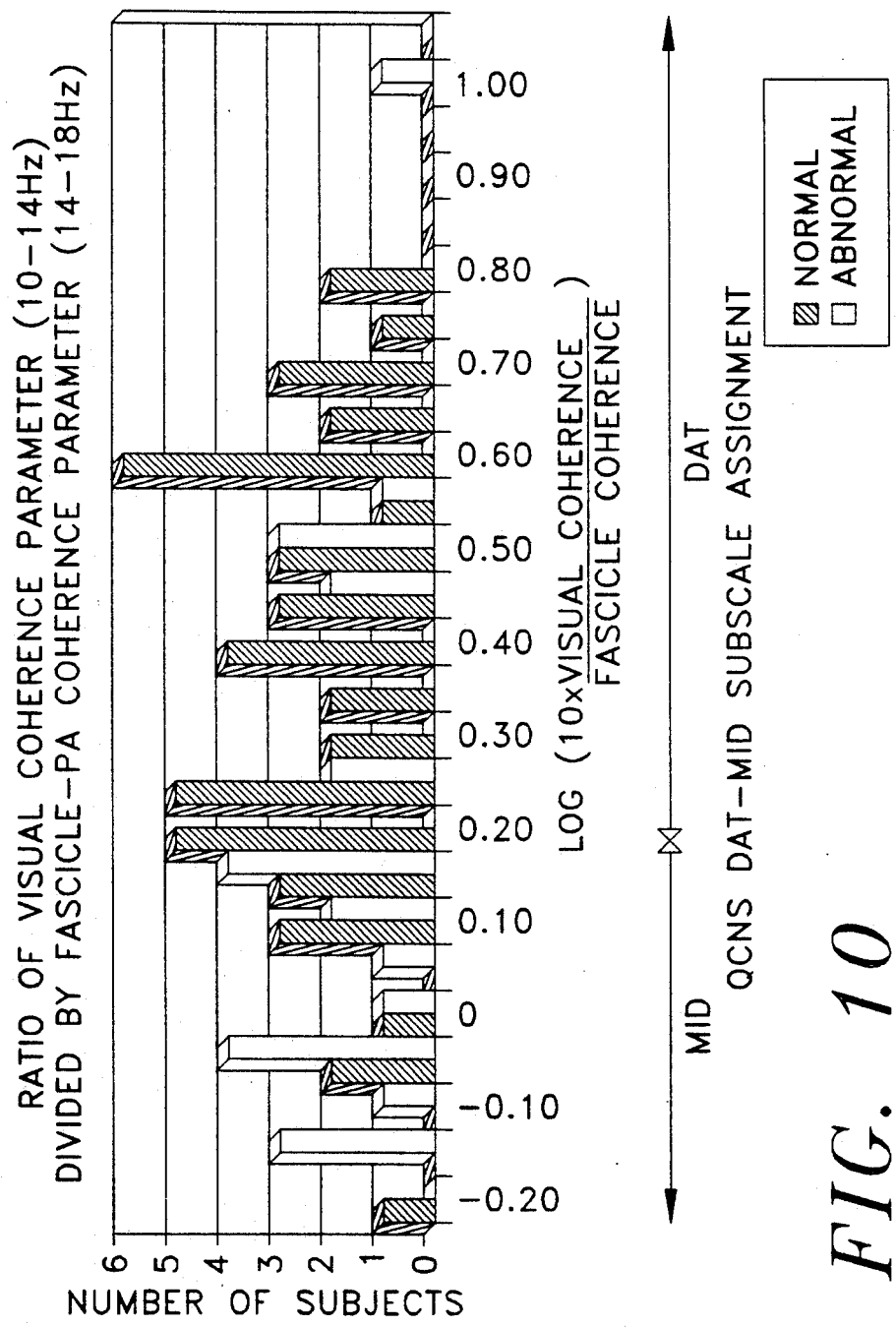

\*\*— difference between DAT and CON $p<0.01$
\*\*\*— difference between DAT and CON, $p<0.005$
+— difference between DAT and MID, $p<0.05$ FIG. 10 is a histogram representing the ratio of VISUAL coherence in the 10-14 Hz band relative FASCICLE-PA coherence in the 14-18 Hz band, and permits a determination of the likelihood of DAT and MID syndromes existing in an individual.

Figure 11A:
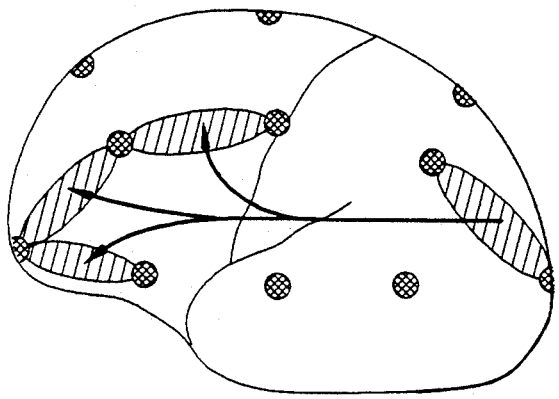
Figure 11B:
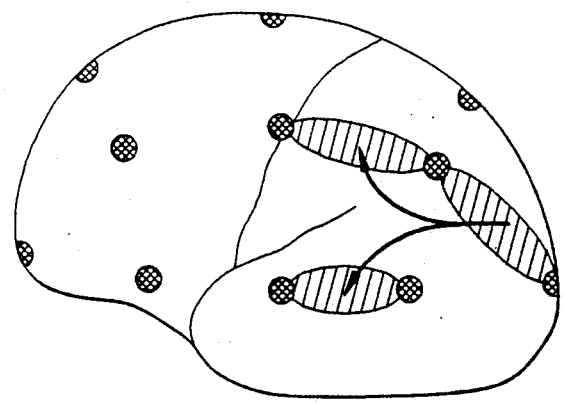

FIG. 11 is a representation of the electrode sites for the mean coherence calculations represented in FIGS. 6-10. Coherence variables were grouped in two combinations, (a) FASCICLE-PA and (b) VISUAL. EEG data were analyzed for indicated electrode pairs (the electrodes linked by shaded ellipses), and mean coherence values were calculated between the pairs that followed known white-matter tracts (depicted by heavy arrows); these coherence values were averaged to measure mean coherence associated with each tract. For clarity, only left hemispheric groupings are shown; homologous groupings for the right hemisphere also were used.

Figure 12:
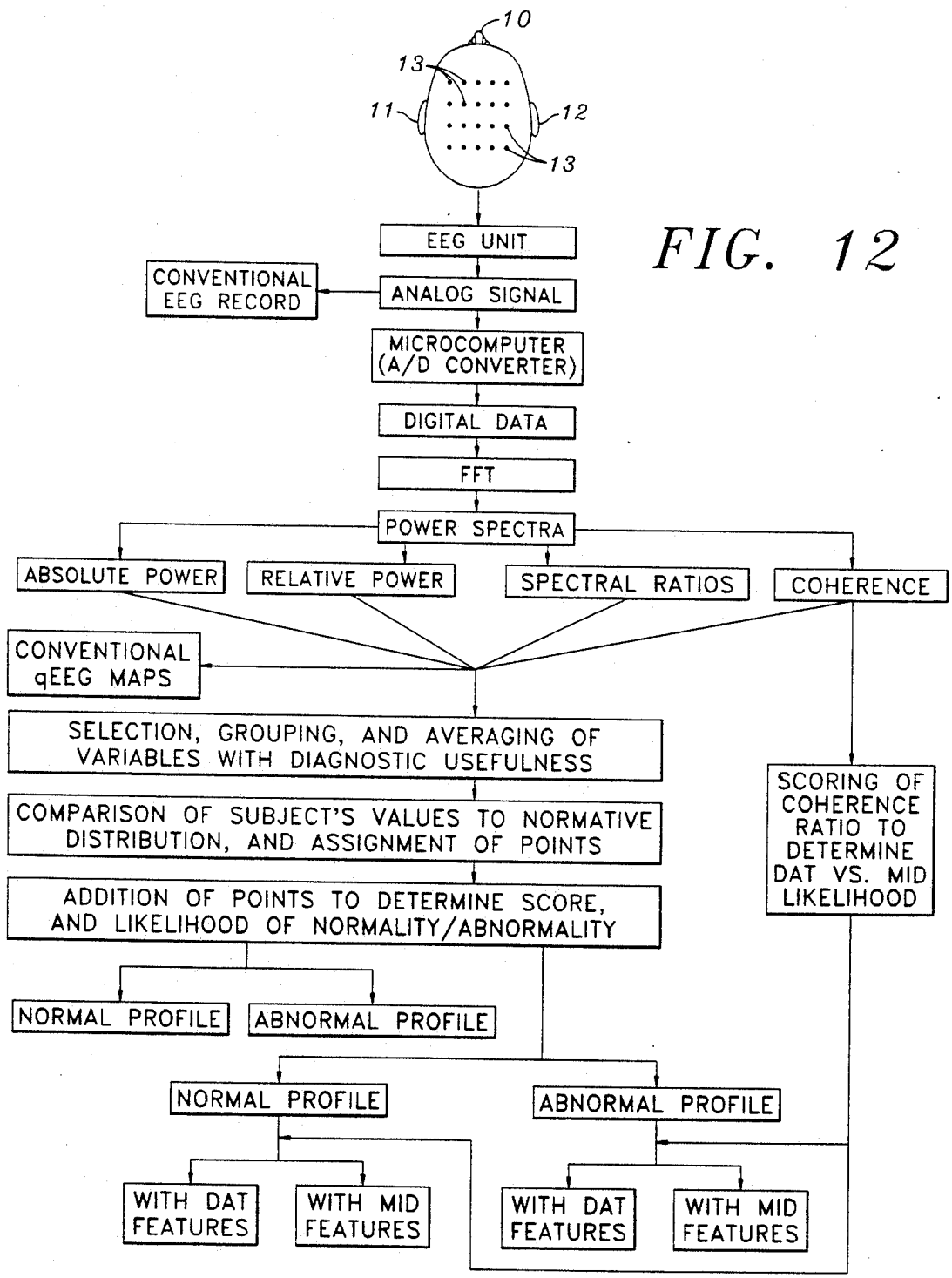

FIG. 12 is a schematic of major components illustrating the data processing and flow to obtain measures of absolute power, spectral ratio, coherence values and for applying the relationship between selected scores to obtain evaluations of brain conditions.

Figure 13:
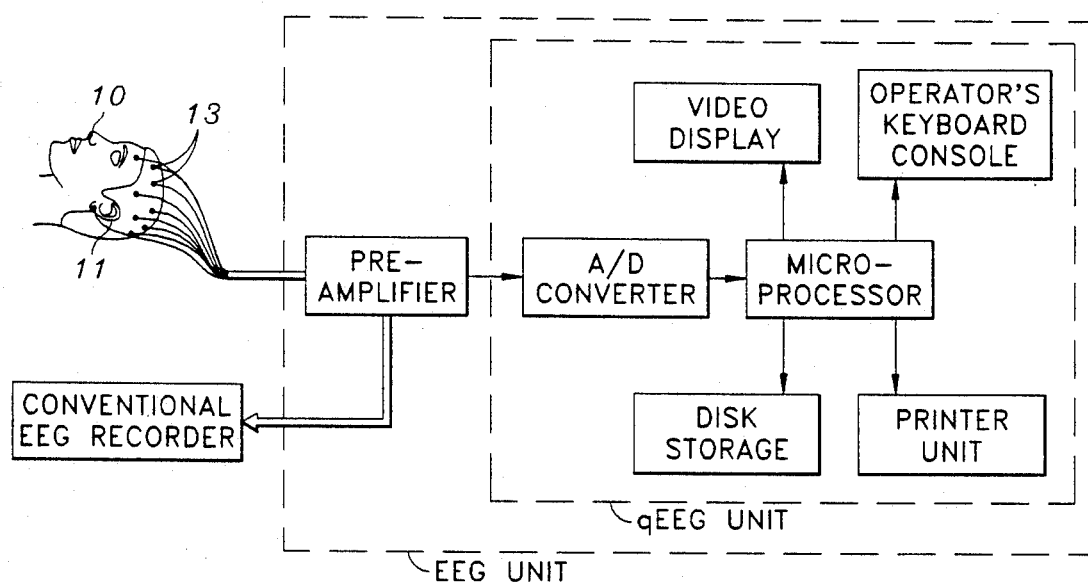

FIG. 13 is a block schematic illustrating the relationship of a patient relative to apparatus for obtaining measures of absolute power, spectral ratio, coherence values and for applying the relationship between selected scores to obtain evaluations of brain conditions.

DESCRIPTION

Figure 1:
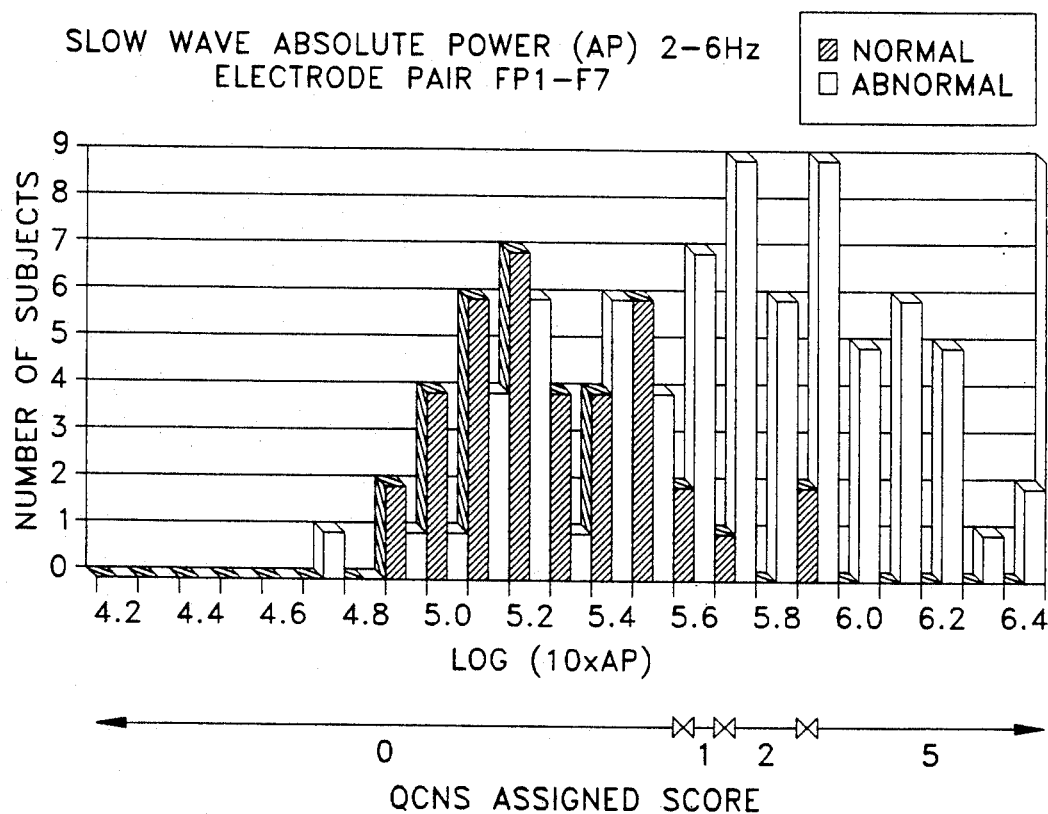
FIG. 1 is a histogram of representative normal and abnormal subject data of first slow wave absolute power data between the 2 to 6 Hz range from electrode pair FP1-F7 near the front of the head after log transformation. The selected predetermined scores are illustrated between the values of 0, 1, 2 and 5.
Figure 2:
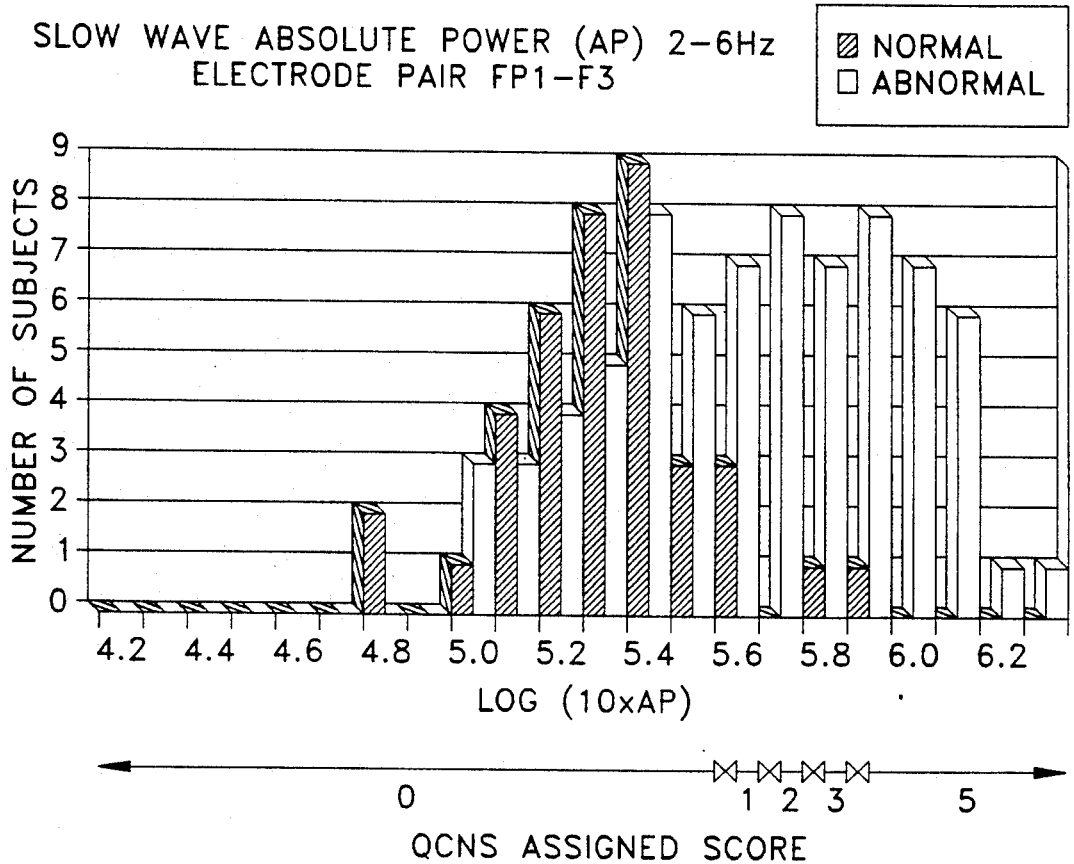
FIG. 2 is a histogram of representative normal and abnormal subject data of second slow wave absolute power data between electrode pair FP1-F3 near the front of the head after log transformation. The selected predetermined scores are illustrated between the values of 0, 1, 2, 3 and 5.
Figure 3:
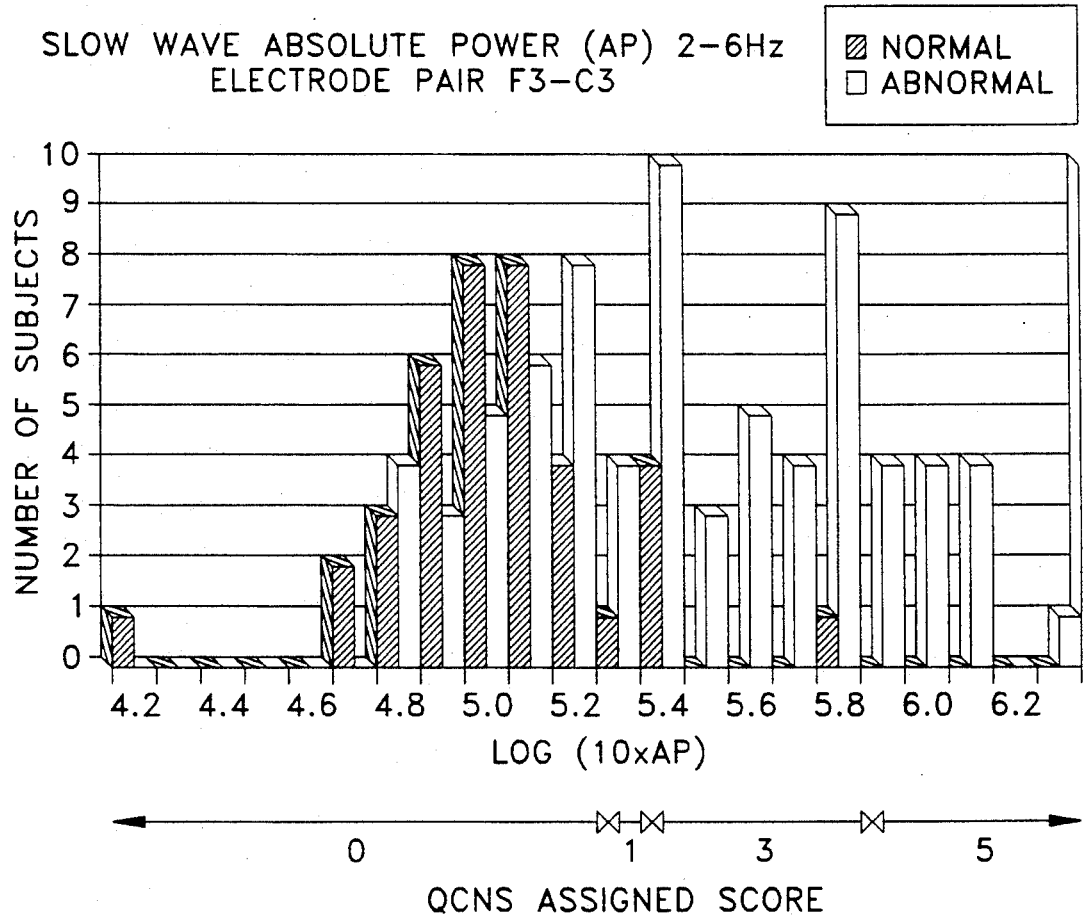
FIG. 3 is a histogram of representative normal and abnormal subject data of third slow wave absolute power data between the 2 to 6 Hz range from electrode pair F3-C3 near the front of the head after log transformation. The selected predetermined scores are illustrated between the values of 0, 1, 3 and 5.

Determining the likelihood of a brain condition of the human comprises determining seven measures of electrical output of the brain region in the head of the subject. These seven measures include the three absolute powers from the front of the head in a low frequency band (2-6 Hz) as discussed with reference to FIGS. 1 to 3. Also measured are two spectral ratios at the back of the head as described with reference to FIGS. 4 and 5. This is the ratio of power in a high frequency band relative to a low frequency band. A determination also is made of the coherence values between anterior and posterior regions of the head, namely the FASCICLE-PA measure as described with reference to FIGS. 6 and 7. Coherence values also are obtained in the posterior head region, namely the VISUAL measure, as described with reference to FIGS. 8 and 9.

FIG. 12 outlines the methods for collection and analysis of data. The head of the subject is shown, with the subject's nose 10 in relation to the left ear 11 and right ear 12. The electrodes 13 are generally illustrated. Different channels are constituted between two selected electrodes 13 as is common in the art.

Conventional EEG data are digitized and processed using a Fast Fourier Transform (FFT) to obtain power spectra. From the power spectra, many variables may be derived, and many of these may have diagnostic usefulness. The variables with diagnostic usefulness which were utilized are absolute power from several frontal sites, spectral ratios from several posterior sites, coherence between several posterior sites, and coherence between anterior and posterior sites. Power, spectral ratio, and coherence values from several different frequency bands may be useful. Absolute power from the 2-6 Hz band, spectral ratios between the 18-22 Hz/2-6 Hz bands, and coherence in the 6-10, 10-14, 14-18, and 18-22 Hz bands were utilized. These bands may be 4 Hz in width, as used, or wider or narrower bands.

In FIG. 13, there is illustrated a sample EEG unit. The electrode head box is shown connected with the head of the patient whereby electrical measurements are taken by electrodes 13 from the brain of the patient. These are fed to the preamplifier and from such an amplifier, conventional EEG data are recorded. This constitutes a conventional EEG unit. Specialized within that construction are the elements for a qEEG unit. Data from the preamplifier are directed to the analog-to-digital converter and, in turn, to a microprocessor. The processor is operated by a keyboard console and the output is directed to a video display, storage or printer unit. The microprocessor operates to generate the appropriate power spectra, spectral ratios, and coherence values, for instance, as indicated in FIGS. 1 to 10.

The selected data variables of absolute power, spectral ratio, and coherence, are grouped and averaged in ways to increase their diagnostic usefulness, and the values from each subject compared with those for a group of normal control subjects. Points are assigned for deviation from the lowest percentiles of this distribution. For example, 0 is assigned for a value below the 40th percentile and represents normal. Points 1, 2, or 3 are assigned for values that are between the 40th and 100th percentile and 5 points is assigned for a value that is greater than that of any normal subject. The point assignment establishes the QCNS.

The points assigned for each variable are summed and a total QCNS score calculated. Total scores of 3 or below indicate a high likelihood of normal brain function, and scores of 4 or greater indicate a high likelihood of abnormal brain function.

In addition to being classified as normal or abnormal, subjects may be classified as having electrophysiological characteristics of the DAT or MID syndromes. This is obtained by examining a ratio of coherence between the front and back of the head to coherence between points in the back of the head.

An analysis of the data to obtain diagnostic information follows. Selected scores are allocated to each of the electrical outputs and spectral ratios as indicated.

The scores are applied in a relationship such that a diagnostic evaluation of the brain condition can be effected. By this is meant a determination may be made between a normal brain condition and an abnormal brain condition. The coherence values allow for determining the likely contribution of DAT and MID disease processes.

The selected scores are such that predetermined integers are chosen having the values of 0, 1, 2, 3 and 5. A score of 0 denotes a normal value; a score of 5 is representative of abnormality (dementia); middle integers represent intermediate departures from a normal brain condition. The scores of the absolute power electrical output, spectral ratios, and coherence are added to make the determination between normal and abnormal. Separately, the coherence values are compared to provide the distinction between DAT and MID.

Diagnosis of Dementia

In determining the likelihood of diagnoses of organic mental syndromes among elderly subjects, data were examined from 49 subjects with clinically diagnosed mild-to-moderate dementia of the Alzheimer's type (DAT), 25 with mild-to-moderate multi-infarct dementia (MID), and 38 elderly controls (CON). EEGs on these 112 subjects were performed by trained technicians using standard clinical procedures. Electrodes were applied according to the International 10-20 System of electrode placement. The EEG was recorded with a Nihon-Kohden 4317 electroencephalograph. Sixteen channels of EEG data were collected in the eyes-closed, maximally alert state using a montage of four longitudinal electrode chains (two temporal, two parasagittal), designed to sample brain electrical activity in all major regions: Fp2-F8, F8-T4, T4-T6, T6-O2, Fp1-F7, F7-T3, T3-T5, T5-O1, Fp2-F4, F4-C4, C4-p4, p4-O2, Fp1-F3, F3-C3, C3-p3, and P3-O1. Eye movements were monitored with anterior scalp electrodes and a right infraorbital electrode referenced to the right ear.

Five minutes of qEEG data were collected from each subject while they rested in the eyes-closed, maximally alert waking state. Data were collected for 32-second periods of time; at the end of each period, data collection was suspended and the patient was vigorously re-alerted. If drowsiness occurred during a 32 second period, data collection was suspended immediately and the patient re-alerted at that time.

Data were digitized and analyzed using the FACT system (for Frequency And Coherence Topography) described previously (Andrew Leuchter, M.D., James E. Spar, M.D., Donald Walter, M.D., et al., "Electroencephalographic Spectra and Coherence in the Diagnosis of Alzheimer'sType and Multi-infarct Dementia," in *Archives of General Psychiatry*. Vol. 44: November, 1987, pp. 993–998. Sixteen channels of data were digitized at a rate of 128 points/channel/second in 4-second epochs. Epochs contaminated by muscle, eye movement, or other artifacts, or by the appearance of drowsiness were eliminated. The first nine 4-second epochs (a total of 36 seconds) of artifact-free data were processed and averaged to obtain a frequency spectrum for that individual.

EEG power values were calculated for each of five frequency bands (each 4 Hz wide) between 2 and 22 Hz (2–6 Hz, 6–10 Hz, 10–14 Hz, 14–18 Hz, and 18–22 Hz). The power in the 0–2 Hz band was excluded from further analysis because of the possibility of this being contaminated by subtle eye movement or other motion artifact. Power above 22 Hz was discarded because of the low proportion of power contained in these bands.

Two different types of power measures were examined: absolute power (measured in microvolts squared), and ratios of power between different bands (spectral ratios). While ratios between any bands could be examined, ratios between high- and low-frequency bands were selected because these were the most useful. Absolute power was calculated for each of the 16 EEG channels in each of five frequency bands between 2–22 Hz. Spectral ratios were calculated for each channel in which the denominator was power in the 2–6 Hz band, and the numerator was power in each band of higher frequency. Coherence was calculated between pairings of channels in the same five frequency bands. Logarithms of the absolute power, spectral ratio, and coherence variables were used to minimize problems with skewness and kurtosis (V.E. Pollock, L.S. Schneider and S.A. Lyness, "EEG amplitudes in healthy, late-middle-aged and elderly adults: normality of the distributions and correlations with age," in *Electroencephalography and Clinical Neurophysiology*. Vol. 75: 1990, pp. 276–288.

Differences among the three groups of subjects, and between the two groups of demented subjects, were examined using analysis of variance for power variables, and t-tests for coherence variables. The magnitude of the F statistic for each variable was noted, since those variables with the highest F statistics show the largest observed group differences (BMDP Biomedical Computer Programs, 1988). For coherence measures, the t-tests that showed the most significant intergroup differences were noted. The t-test is a method for comparing the means of two samples to determine whether there is a statistically significant difference. The F statistic is a comparable method that may be used for two or more groups.

Using absolute power measures, the 2-6 Hz band (a mixed delta and theta band) showed the largest power differences among the three groups of subjects, with F statistics from all channels greater than 9. The highest F values were found for channels in the anterior regions, and the channels and frequency bands with the highest F statistics were identified and selected for use in the QCNS.

Spectral ratios showed more consistent differences between demented and non-demented subjects than did power measures. 93% of all these variables had F statistics greater than 4.0. The highest F values were seen for channels in the posterior regions, and in frequency bands above 14 Hz.

The specific channels and frequency bands with the highest F statistics were identified and selected for use in the QCNS (FIGS. 1-5). Neither power measures, nor 2-6 Hz based spectral ratios differentiated the DAT and MID groups.

DAT and MID Diagnosis

Clinical and neuropathological evaluation of elderly subjects with dementia has traditionally concentrated upon the focal distribution of brain disease, ignoring changes in the complex connections that link brain areas and that are crucial for cognition. Therefore, regional measures of power and spectral ratios have been used, while measures of activity shared between brain regions (i.e., coherence) largely have been ignored.

The invented QCNS system uses electroencephalographic coherence as well as regional power measures to examine the effects of organic brain disease in general, and DAT and MID in particular, on the functional connections between brain areas.

Coherence between brain areas known to be linked by two different types of connections were studied. First, dense narrow bands of long corticocortical fibers, and second, broad complex networks of corticocortical and cortico-subcortical fibers were examined. The coherence variables used in the QCNS were selected based on the differing neuropathology of DAT and MID. Specific connections between brain regions are affected primarily in each illness (and largely spared in the other illness). DAT and MID showed significantly differing patterns of coherence.

In Alzheimer's disease, a group of DAT subjects showed selective decreases in coherence between areas that are connected by dense corticocortical fibers. These fibers should be systematically "disconnected" by the neuropathology of DAT, and less affected by the nonspecific damage and demyelination of MID.

Conversely, the MID group showed changes in coherence where complex networks of connections involving corticocortical, corticostriate, and corticothalamic fibers are responsible for linking brain areas. These networks, reliant on large volumes of white matter and involving loops of connections between cortical and subcortical structures, were more sensitive to disruption by the subcortical vascular damage of MID.

Coherence between pre- and post-Rolandic areas (linked by long corticocortical fibers) and coherence within pre- and post-Rolandic areas (linked by complex networks of connections) were examined. The coherence between areas separated by the Rolandic fissure decreased primarily among DAT subjects, while coherence within preor post-Rolandic networks decreased primarily among MID subjects.

A paradigm of averaging coherence among multiple recording sites that overlie the distribution of known corticocortical fibers to measure the electrical activity transmitted through those fibers was used. This paradigm was used to monitor the functional integrity of the two major classes of cortical connectivity: long dense corticocortical fiber tracts (exemplified by the superior longitudinal fasciculus), and complex networks of corticocortical and cortico-subcortical fibers (exemplified in the post-Rolandic area by the projections of the visual pathway, and in the pre-Rolandic area by the projections of the prefrontal cortex).

Coherent brain electrical activity mediated by these fiber tracts was measured. The cortical distribution of the tracts on the convexities of the brain in relation to EEG electrode position was first approximated. For example, the superior longitudinal fasciculus (SLF) connecting the parietal cortex primarily underlying electrode P3 with the cortex underlying the anterior electrodes Fp1, F3, and F7 on the left (and electrode P4 with the anterior electrodes Fp2, F4, and F8 on the right) was estimated. A determination was made as to which pairs of EEG channels most closely approximate this distribution. These pairs were averaged to determine the "mean coherence" transmitted by the SLF in the posteroanterior (FASCICLE-PA) direction. The pairings of channels chosen to represent FASCICLE-PA and the visual pathway (VISUAL), are listed in TABLE I and are shown graphically in FIG. 11.

TABLE I

| Anatomic Pathway (Abbreviation) | Electrode(s) of origin | Electrodes of termination | Averaged channel pairings |
|---|---|---|---|
| Superior longitudinal fasciculus -- posteroanterior projection (FASCICLE-PA) | P3 (left) 01 | F3, Fp1, F7, C3 | P3-01/F3-C3 P3-01/Fp1-F3 P3-01/Fp1-F7 |
|  | P4 (right) 02 | F4, Fp2, F8, C4 | P4-02/Fp2-F4 P4-02/Fp2-F8 P4-02/F4-C4 |
| Visual pathway projections (VISUAL) | 01 (left) | P3, C3, T3 and T5 | P3-01/P3-C3 P3-01/T3-T5 |
|  | 02 (right) | P4, C4, T4 and T6 | P4-02/P4-C4 P4-02/T4-T6 |

Cortical areas that were linked by dense narrow bands of long corticocortical fibers (primarily the superior longitudinal fasciculus) showed significantly diminished coherence in subjects with DAT; among MID subjects, this coherence was not significantly affected (FIG. 7). Areas that were linked by broad connective networks (primarily the projections of the visual pathway) showed the largest decreases in coherence among MID subjects (FIG. 9). These findings are consistent with neuropathologic evidence that Alzheimer's disease is a neocortical "disconnection syndrome" in which there is a loss of structural and functional integrity of long corticocortical tracts. The findings further suggest that the vascular disease of MID most prominently affects broad fiber networks, that may be more vulnerable to diffuse subcortical vascular damage. These results indicate that electroencephalographic coherence detects basic pathophysiologic differences between subjects with DAT and MID.

Some changes in coherence were prominent in both DAT and MID subjects, such as those seen in the VISUAL measure at 6-10 Hz and those seen in the FASCICLEPA measure at 14-18 Hz. These features were incorporated into the basic QCNS, and help in a determination of the likelihood of normality/abnormality. Other coherence variables were more specific for disease state, such as VISUAL coherence in the 10-14 Hz band for MID and FASCICLE-PA coherence in the 14-18 Hz band for DAT. These latter two variables were combined in a ratio and used for determining the likelihood that an individual had characteristics of DAT or MID. This ratio showed significant differences between DAT and MID subjects (FIG. 10).

The QCNS

QCNS is based on identifying those variables that showed the greatest differences among groups of subjects, and utilizing those that showed a large amount of group separation. If a number of such variables are chosen, they could each describe different neurophysiologic facets of a condition. A method for describing the total abnormality on multiple parameters yields more diagnostically useful information.

If in any given distribution of a variable A, where changes in the quantity of that variable present in the individual are associated with a disease syndrome, a deviation of the quantity in a given direction (either an increase or a decrease) increases or decreases the likelihood that a given disease is present in that individual. The direction that is associated with the disease is termed "pathologic" and the direction associated with the control condition is termed "control."

There also exist median values for this variable for both pathologic and control states. The greater the deviation of the variable in the control direction, the greater the likelihood that the condition of interest does not exist in that individual. The greater the deviation in the pathologic direction, the greater the likelihood that the condition exists.

Several critical points may be chosen empirically as thresholds where the likelihood of the condition existing change. At each of these thresholds, a change in the probability is indicated by the assignment of increasing "points." The larger the number of points, the greater the likelihood of abnormality. For example, if the value of the variable tends strongly in the control direction, no points are assigned. If, however, the value approaches the median for the controls, but does not exceed the median, a single point might be assigned (this signifies a low but definite probability of abnormality). When the median value for the controls is crossed in a pathologic direction, the probability would increase again, and two points are assigned.

Other critical thresholds could be assigned at any percentile of the normal distribution. The maximum number of points might be assigned when the value of the variable is beyond that for any control subject in the pathologic direction. By summing the points assigned for several such variables, a cumulative risk for the existence of a pathologic condition is assigned.

The power, spectral ratio, and coherence variables that detected the largest intergroup differences were integrated into the Quantitative Cerebral Neurophysiology Scale (QCNS). The QCNS uses a model of the decision-making process employed by psychiatric encephalographers in evaluating EEG records of elderly subjects. Thus, the presence of abnormal features results in the accumulation of "points," as a way to capture degrees of abnormality. If a subject exhibits an excessive degree of abnormality (high score), the subject's record is associated with the pattern of abnormality most representative of a known diagnostic entity. This model permits the choice of design parameters to reflect a balance between the clinical objectives of simplicity, reliability, and applicability (Cook, I.A. Computeraided evaluation of early neoplasms. Dissertation submitted for M.D. degree. Yale University, New Haven, CT, 1987).

The variables in the QCNS included: (a) slow wave absolute power data (2-6 Hz) from channels near the front of the head, (b) slow wave ratios (18-22 Hz / 2-6 Hz power) from channels near the occiput, and (c) coherence values measured for the VISUAL aggregate (6-10 and 10-14 Hz bands) and the FASCICLE-PA aggregate (14-18 Hz band).

Slow wave absolute power values were taken from Fp1-F7, Fp1-F3, and F3-C3 pairings, and slow wave ratios were calculated from measurements at the P3-O1 and P4-O2 channels.

The VISUAL coherence aggregate assesses the functional connectivity among the post-Rolandic regions in the posterior cortex and reflects the average of coherence values between the P3-O1 channel and C3-P3 and T3-T5 channels (and the homologous pairings for the right hemisphere).

The FASCICLE-PA variable assesses integrity of long fiber tracts mediating communication between preand post-Rolandic regions (e.g. via the superior longitudinal fasciculus) by averaging coherence values between the P3-O1 channel and the Fp1-F7, Fp1-F3, and F3-C3 channels, and their right hemisphere homologs. I5 All power values and coherence values were multiplied by ten and log transformed to minimize skewness and kurtosis. Calculation of each variable is given in TABLE II.

For each variable, a normal range first was established from an extensive examination of data from elderly individuals in unimpaired and diseased states (FIGS. 1-6, 8, 10). Values outside of these ranges were deemed abnormal and were assigned a score (TABLE II). The number of points given for each abnormal parameter depends upon the magnitude of the departure from normal (1 point if beyond the 40th percentile of the abnormal value range, 2 points if beyond the median value, 3 points if the value was beyond the 97% specificity level, and 5 points if beyond any overlap with the normal subject range, i.e., 100% specific). Not all the variables have a 2, 3 or 5 point score allocated to each variable as indicated in Table II. The values set out in Table II are system and equipment dependent. Conversion factors may be applied as necessary for different equipment.

TABLE II

| Variable | Calculation | QCNS Assigned Score | | | |
|---|---|---|---|---|---|
| | | 1 | 2 | 3 | 5 |
| Slow wave absolute power (AP) | log (10 × AP) | >5.687 | >5.760 | | >5.9569 |

TABLE II-continued

| Variable | Calculation | QCNS Assigned Score 1 | 2 | 3 | 5 |
|---|---|---|---|---|---|
| 2-6 Hz, electrode pair FP1-F7 Slow wave absolute power (AP) | log (10 × AP) | >5.601 | >5.747 | >5.804 | >5.962 |
| 2-6 Hz, electrode pair FP1-F3 Slow wave absolute power (AP) | log (10 × AP) | >5.396 | | >5.435 | >5.980 |
| 2-6 Hz, electrode pair F3-C3 | | | | | |
| Slow wave ratio of AP 18-22 Hz/2-6 Hz, electrode pair P3-O1 | $\log\left(10 \times \frac{AP_{18-22Hz}}{AP_{2-6Hz}}\right)$ | <0.466 | | <0.329 | <0.068 |
| Slow wave ratio of AP 18-22 Hz/2-6 Hz, electrode pair P4-O2 | $\log\left(10 \times \frac{AP_{18-22Hz}}{AP_{2-6Hz}}\right)$ | <0.445 | | <0.227 | <0.071 |
| FASCICLE -PA (coherence (c)) (Long fiber tracts) | log (10 × C) | <0.140 | | <0.080 | <−0.131 |
| VISUAL (coherence (c)) (posterior cortex) | log (10 × C) | <0.47 | | <0.28 | |

When an individual attained a total (cumulative) score above the designated threshold (greater than 3 points), the qEEG was classified as abnormal.

A second analysis can be performed to assess whether the data are more like that seen in subjects with DAT or with MID. This was determined by comparing the values of the VISUAL and FASCICLE-PA coherence measures in a ratio. Diminished fascicular coherence is characteristic of DAT while diminished posterior coherence is associated with MID. The higher ratio values suggested a DAT-like process, while lower values suggested a contribution of vascular pathology such as that seen in MID.

The ratios are calculated as follows:

DAT-MID subscale value =

$$\log\left[10 \times \frac{\text{(VISUAL coherence at 10-14 Hz)}}{\text{FASCICLE-}PA \text{ coherence at 14-18 Hz)}}\right]$$

If the ratio is greater than 0.18, then the pattern is more like DAT. If the ratio is less than or equal to 0.18, then the pattern is more like MID.

QCNS distinguished subjects with DAT, MID, and normal controls with a specificity of 82% and sensitivity of 81% in the identification of dementia. For less impaired subjects (Mini Mental State Examination score, or MMSE, ≥20), sensitivity fell to 72%; for more impaired subjects (MMSE <20), sensitivity increased to 89%.

The sensitivity and specificity of the QCNS were evaluated on an independent, cross-validation sample of 61 subjects Twenty-nine of these subjects had DAT or MID, 9 had delirium, and the remainder were a clinically heterogeneous group of subjects without dementia (6 with major depressive episode, 5 normal controls, and 12 with age-associated memory impairment or AAMI). The QCNS shows a specificity of 74% and sensitivity of 79% in identifying impairment among this second set of subjects, accurately separating those with dementia and delirium from those without clear organic impairment. The QCNS showed a moderate association with mental status as measured by the MMSE, and with functional status as measured by the Blessed Dementia Scale.

These results indicate that the QCNS is a clinically useful measure of the neurophysiologic changes accompanying dementia in the elderly.

Determining Likelihood of DAT and MID Syndrome

The ratio of FASCICLE-PA to VISUAL coherence was examined as a subscale score for predicting the clinical probability of DAT or MID. This is a probabilistic determination, in which patients with the clinical feature of DAT or MID may have either or both disease processes present and contributing to their cognitive losses. This DAT-MID subscale of the QCNS is designed to reflect the probability that one or another syndrome may be present and contributing to symptoms in an individual case. Ranges for "probable" and "possible" DAT have been designated to indicate the likelihood that a degenerative illness may be present in an individual case. This may, in fact, be any process that has caused neurophysiologic disturbances similar to DAT, and DAT may not be the only problem present in the situation. Similarly, ranges for "possible" and "probable" MID have been designated indicating the likelihood that cerebrovascular disease may be associated with cognitive loss in an individual case as a sole or contributing factor.

In the original sample of demented subjects, 83% of the subjects in the "probable DAT" range (subscale score of >0.50) had clinically diagnosed DAT, 85% of the subjects in the "possible DAT" range (subscale score >0.18 and <0.51) had clinically diagnosed DAT, 62% of the subjects in the "possible MID" range (subscale score >0 and ≤0.18) had clinically diagnosed MID, and 67% of the subjects in the "probable MID" range (subscale score <0) had clinically diagnosed MID.

Although there was no group of subjects with "mixed" dementia in this sample, it might be reasonable to presume that subjects in the "possible" categories would have a higher likelihood of having mixed disease (i.e., losses due to coexistence of DAT and MID) than those in the probable categories. Furthermore, there could be categories of possible or probable abnormality on the basic QCNS as well, indicating the likelihood that a subject has normal or abnormal brain function. There could also be constructed subscales that indicate the relative likelihood that any given syndrome such as depression, delirium, or another diagnosable mental illness exists in an individual.

GENERAL

Although the invention has been described with reference to dementia, applications beyond that brain condition are possible. For instance, other brain conditions such as depression and delirium have been examined by this procedure.

The cross-validation of the QCNS on subjects with a variety of conditions including depression, delirium, and AAMI (thought to represent memory loss in old age that does not necessarily reflect a disease condition) suggest that the QCNS may be useful in differentiating conditions that present with similar symptoms. For example, individuals with AAMI, DAT, or MID all may come to medical attention with primary complaints of memory loss. The QCNS, applied on a single or on multiple occasions, may be useful in determining the likelihood that this symptom is associated with a degenerative brain disease.

Other conditions, such as severe anxiety states, drug intoxications, or metabolic derangements also may present with similar symptoms, and the QCNS may be useful in identifying these conditions when present.

Moreover, although the data used in the scoring have been obtained from absolute power values from EEG, it is possible that other values of electrical output can be used. Electrical output is an energy measurement, and can be obtained from different selected electrodes about the head. Different channels can be used. The electrodes do not necessarily have to be those in the front of the head. Furthermore, different frequency bands can be used.

Similarly, instead of the spectral ratios at the back of the head, a different ratio can be used. This could be a ratio between high-frequency power from one brain location, and low-frequency power from another location. Different frequency bands in the delta, theta, alpha and beta regions can be employed.

Coherence values can be obtained from different areas of the head. Other than those described, these could be coherence between hemispheres, or coherence following any other known neuroanatomic tracts. Furthermore, the brain electrical activity in response to specific stimuli (i.e., event-related potentials or taskactivated EEG) may be useful under some circumstances.

QCNS identifies parameters that are likely to yield information that would be useful in identifying individuals with different psychiatric syndromes. DAT and MID were chosen because the neuropathology of these illnesses are relatively well understood, and both the conventional EEG and qEEG are well-known to be abnormal in these groups. The abnormalities are nonspecific, however, and no single parameter has been shown to accurately identify a majority of persons with either condition. This probably is the case since one variable described only a single neurophysiologic facet of an illness.

The QCNS approach may be generalized to other pathologic and non-pathologic conditions, and may be used to yield a likelihood for discriminating between two pathological conditions or between two physiologic states in a given individual. It also may be used to help chart the normal development of an individual, or the evolution of a disease process.

In some cases, it may only be necessary to diagnose whether the dementia is DAT or MID. In other cases, it may be necessary to use the diagnosis to determine between normal and abnormal prior to being specific about the nature of the abnormality. Moreover, although particular selected integers have been used, it is possible that other selected integers could be effective. Also, in place of adding all the integers, a different form of relationship between these integers can be established to provide diagnostic information.

Selected electrical outputs, spectral ratios and coherence values can be used and suitably scored to apply a relationship to give the diagnostic evaluation.

Different names may be assigned to different ranges of QCNS scores, indicating the likelihood that any particular score is associated with abnormality. For example, rather than having cutoffs for "normal" and "abnormal," one could assign ranges of "possible" or "probable" normality or abnormality depending on the score. Many different such ranges could be assigned depending on the age of the subjects, the illnesses involved, and other factors.

Many other forms of the invention exist, each differing from the other in matters of detail only. The invention is to determined by the scope of the appended claims.

We claim:

1. A method of diagnosing a brain condition in a human comprising applying electrodes from an EEG unit about the head of a human, determining from the electrodes at least one measure of an electrical signal output of a brain region in the head of a subject, determining at least one spectral ratio of a brain region in the head of the subject, determining at lest one coherence value of a brain region, applying a relationship between the electrical signal output, spectral ratio and coherence as a diagnostic evaluation of the brain condition, and presenting such relationship.

2. A method as claimed in claim 1 including determining at least three measures of the electrical signal output of brain regions.

3. A method as claimed in claim 2 including determining at least two spectral ratios of brain regions.

4. A method as claimed in claim 3 including allocating selected scores to each of the electrical signal output, spectral ratios, and coherence and applying a relationship of the scores as the diagnostic evaluation of the brain condition.

5. A method as claimed in claim 4 including allocating selected scores to each of three electrical signal outputs, two spectral ratios and two coherence values, and applying the relationship of the scores as the diagnostic evaluation.

6. A method as claimed in claim 5 wherein the score is related to normal and abnormal brain conditions respectively and wherein the scores are a predetermined number of selected integers, and wherein the highest integer represents an abnormal brain condition, the lowest integer represents a normal brain condition, and middle integers are selected to represent a selected measure of departure from a normal brain condition, and wherein the scores representative of electrical signal output, spectral ratio, and coherence are added to provide a diagnostic evaluation of the brain condition.

7. A method as claimed in claim 2 including allocating selected scores to each of the electrical signal output, spectral ratios, and coherence and applying a relationship of the scores as the diagnostic evaluation of the brain condition.

8. A method as claimed in claim 7 wherein the score is related to normal and abnormal brain conditions respectively and wherein the scores are a predetermined number of selected integers, and wherein the highest integer represents an abnormal brain condition, the lowest integer represents a normal brain condition, and middle integers are selected to represent a selected measure of departure from a normal brain condition, and wherein the scores representative of electrical signal output, spectral ratio, and coherence are added to provide a diagnostic evaluation of the brain condition.

9. A method as claimed in claim 4 wherein the score is related to normal and abnormal brain conditions respectively and wherein the scores are a predetermined number of selected integers, and wherein the highest integer represents an abnormal brain condition, the lowest integer represents a normal brain condition, and middle integers are selected to represent a selected measure of departure from a normal brain condition, and wherein the scores representative of electrical signal output, spectral ratio, and coherence are added to provide a diagnostic evaluation of the brain condition.

10. A method as claimed in claim 1 including determining at least two measures of spectral ratio of brain regions.

11. A method as claimed in claim 3 including allocating selected scores to each of the electrical signal output, spectral ratios, and coherence and applying a relationship of the scores as the diagnostic evaluation of the brain condition.

12. A method as claimed in claim 11 wherein the score is related to normal and abnormal brain conditions respectively and wherein the scores are a predetermined number of selected integers, and wherein the highest integer represents an abnormal brain condition, the lowest integer represents a normal brain condition, and middle integers are selected to represent a selected measure of departure from a normal brain condition, and wherein the scores representative of electrical signal output, spectral ratio, and coherence are added to provide a diagnostic evaluation of the brain condition.

13. A method as claimed in claim 1 including applying a coherence relationship, together with the electrical signal output and spectral ratio as a diagnostic evaluation between a normal condition and a condition of dementia.

14. A method as claimed in claim 13 including allocating selected scores to each of the electrical signal output, spectral ratio and the coherence, and applying the relationship of the scores as the diagnostic evaluation.

15. A method as claimed in claim 13 wherein the score is related to normal and abnormal brain conditions respectively and wherein the scores are a predetermined number of selected integers, and wherein the highest integer represents an abnormal brain condition, the lowest integer represents a normal brain condition, and middle integers are selected to represent a selected measure of departure from a normal brain condition, and wherein the scores representative of electrical signal output, spectral ratio, and coherence are added to provide a diagnostic evaluation of the brain condition.

16. A method as claimed in claim 1 including allocating selected scores to each of the electrical signal output, spectral ratios, and coherence, and applying a relationship of the scores as the diagnostic evaluation of the brain condition.

17. A method of diagnosing a brain condition in the human comprising applying electrodes from an EEG unit about the head of a human, determining from the electrodes at least three measures of electrical signal output of the brain region in the head of the subject, determining at least two spectral ratios of a brain region in the head of a subject, determining at least two coherence values of a brain region in the head of a subject, allocating selected scores to each of the electrical signal outputs, spectral ratios, and the coherence, the scores being selected integers between 0 and 5, and preferably being 0, 1, 2, 3 and 5, and wherein the lowest integer represents a normal brain condition, the highest integer is representative of an abnormal brain condition indicative of dementia, integers 1 to 3 are representative of varying departures from a normal brain condition, adding the scores from the three electrical signal outputs and the scores from the two spectral ratios and the two coherence values as a determination of the measure of normality or dementia of the subject, and presenting such determination.

18. A method of diagnosing a brain condition in the human comprising applying electrodes from an EEG unit about the head of a human, determining at least one measure of coherence between two brain regions in the head of a subject, applying a coherence value as a diagnostic evaluation of the brain condition thereby to facilitate distinguishing between a dementia condition of the Alzheimer's-type and a condition of multi-infarct dementia, and presenting such coherence value.

19. A method as claimed in claim 18 including allocating selected scores to the coherence value and applying a relationship of the scores as the diagnostic evaluation of the brain region.

20. A method of diagnosing a brain condition in the human comprising applying electrodes from an EEG unit about the head of a human, determining at least two coherence values of a brain region in the head of the subject, the one coherence value being a coherence value within the posterior cortex, and second coherence value being that between the front and the back of the brain, applying a relationship between the values as a diagnostic evaluation of a brain condition of either dementia of the Alzheimer's-type or multi-infarct dementia, and presenting such relationship.

21. A method of diagnosing a brain condition in the human comprising applying electrodes from an EEG unit about the head of a human, determining from the electrodes at least one measure of an electrical signal output of a brain region in the head of a subject, determining at least one spectral ratio of a brain region in the head of a subject, determining at least one coherence value of a brain region in the head of a subject, allocating selected scores to each of the electrical signal output, spectral ratios and coherence values, applying a relationship between the scores and additionally applying a coherence relationship between selected coherence values prior to a further scoring, such selected scores and further scoring being used as a diagnostic evaluation of the brain condition, the evaluation being selectively to distinguish between dementia, nondementia and in the case of dementia, to distinguish between dementia of the Alzheimer's-type and multi-infarct dementia, and presenting such relationship.

22. A method of diagnosing the nature of dementia in a human comprising applying electrodes from an EEG unit about the head of a human, determining from the electrodes at least three measures of electrical signal output of a brain region in the head of a subject, the three measures being absolute power from the front of the head, determining at least two spectral ratios of a brain region in the head of a subject, the spectral ratios being at the back of the head, determining at least two coherence values of the brain region in the head of a subject, the one coherence value being that within the posterior cortex and the other coherence value being that between the front and back of the head, allocating selected scores to each of the electrical signal outputs, spectral ratios and selected coherence values, the scores being predetermined values between a low value and a high value, the low value being representative of normal-type conditions, the high value being representative of dementia, and a middle value being representative of intermediate degrees of abnormality, and wherein additionally a condition is distinguishable between dementia of the Alzheimer's-type and multi-infarct dementia in accordance with the scored coherence values, and presenting the scores.

23. Apparatus for diagnosing a brain condition comprising electrodes from an EEG unit for location about the head of a human, means for determining from the electrodes at least one measure of an electrical signal output of a brain region in the head of a subject, means for determining at least one spectral ratio of a brain region in the head of the subject, means for determining a coherence value, means for applying a relationship between the electrical signal output, spectral ratio and the coherence value as a diagnostic evaluation of the brain condition, and means for presenting such relationship.

24. Apparatus for diagnosing a brain condition as claimed in claim 23 including means for determining at least three measures of the electrical signal output of the brain region.

25. Apparatus for diagnosing a brain condition as claimed in claim 24 including means for determining at least two spectral ratios of the brain region.

26. Apparatus for diagnosing a brain condition as claimed in claim 23 including means for allocating selected scores to each of the electrical signal output, spectral ratios, and coherence, and means for applying a relationship of the scores as the diagnostic evaluation of the brain condition.

27. Apparatus for diagnosing a brain condition as claimed in claim 26 including means for adding the scores representative of electrical signal output, spectral ratio, and coherence, and selectively including means for additionally adding a score of coherence ratio to provide a diagnostic evaluation of the brain condition.

28. Apparatus for diagnosing a brain condition as claimed in claim 24 including means for allocating selected scores to each of the electrical signal output, spectral ratios, and coherence, and means for applying a relationship of the scores as the diagnostic evaluation of the brain condition.

29. Apparatus for diagnosing a brain condition as claimed in claim 28 including means for adding the scores representative of electrical signal output, spectral ratio, and coherence, and selectively including means for additionally adding a score of a coherence ratio to provide a diagnostic evaluation of the brain condition.

30. Apparatus for diagnosing a brain condition as claimed in claim 23 including means for determining at least two measures of spectral ratio of a brain region.

31. Apparatus for diagnosing a brain condition as claimed in claim 30 including means for allocating selected scores to each of the electrical signal output, spectral ratios, and coherence, and means for applying a relationship of the scores as the diagnostic evaluation of the brain condition.

32. Apparatus for diagnosing a brain condition as claimed in claim 31 including means for adding the scores representative of electrical signal output, spectral ratio, and coherence, and selectively including means for additionally adding a score of a coherence ratio to provide a diagnostic evaluation of the brain condition.

33. Apparatus for diagnosing a brain condition as claimed in claim 23 including means for allocating selected scores to each of the electrical signal output, spectral ratios, and coherence, and means for applying a relationship of the scores as the diagnostic evaluation of the brian condition.

34. Apparatus for diagnosing a brain condition as claimed in claim 33 including means for adding the scores representative of electrical signal output, spectral ratio, and coherence, and selectively including means for additionally adding a score of a coherence ratio to provide a diagnostic evaluation of the brain condition.

35. Apparatus for diagnosing a brain condition in a human comprising electrodes from an EEG unit for locations about the head of a human means for determining from the electrodes at least three measures of electrical signal output of the brain region in the head of the subject, means for determining at least two spectral ratios of a brain region in the head of a subject, means for determining two coherence values, means for allocating selected scores to each of the electrical signal outputs, spectral ratios and a coherence values, the scores being selected integers between 0 and 5, and preferably being 0, 1, 2, 3 and 5, and wherein the lowest integer is representative of a normal brain condition, the highest integer is representative of an abnormal brain condition indicative of dementia, and middle integer scores are representative of varying departures from a normal brain condition, means for adding the scores from the three electrical signal outputs, the scores from the two spectral ratios and the coherence values to determine the measure of normality or dementia of the subject, and means for presenting such scores.

36. Apparatus for diagnosing a brain condition comprising electrodes from an EEG unit for location about the head of a human, means for diagnosing a brain condition in a human comprising means for determining from the electrodes at least two coherence values of a brain region in the head of the subject, the one coherence value being a coherence value within the posterior cortex, and second coherence value being the value between the front and the back of the brain, means for applying a relationship between the values as a diagnostic evaluation of a brain condition of either dementia of the Alzheimer's-type or multi-infarct dementia, and means for presenting such relationship.

37. Apparatus for diagnosing a brain condition comprising electrodes from an EEG unit for location about the head of a human, means for diagnosing a brain condition in a human comprising means for determining from the electrodes at least one measure of the electrical signal output of a brain region in the head of a subject, means for determining at least one spectral ratio of a brain region in the head of a subject, means for determining at least two coherence values of a brain region in the head of a subject, means for allocating selected scores to each of the electrical signal output and spectral ratios and a coherence value, means for applying a relationship between the scores and additionally a ratio of coherence values as a diagnostic evaluation of the brain condition, the evaluation being selectively to distinguish between dementia, non-dementia and in the case of dementia, to distinguish between dementia of the Alzheimer's-type and multi-infarct dementia, and means for representing such relationship.

38. Apparatus for diagnosing a brain condition comprising electrodes from an EEG unit for location about the head of a human, means for diagnosing the nature of dementia in a human comprising means for determining from the electrodes at least three measures of electrical signal output of a brain region in the head of a subject, the three measures being absolute power from the front of the head, means for determining at least two spectral ratios of a brain region in the head of a subject, the spectral ratios being at the back of the head, means for determining at least two coherence values of the brain region in the head of a subject, the one coherence value being that within the posterior cortex and the other coherence value being that between the front and back of the head, means for allocating and adding selected scores to each of the electrical signal outputs, spectral ratios and coherence values, the scores being predetermined values between a low value and a high value, the low value being representative of normal-type conditions, the high value being representative of dementia, and the middle value being representative of an intermediate degree of abnormality, including means for obtaining a ratio of coherence values and scoring the ratio wherein a determination of dementia is distinguishable between dementia of the Alzheimer's-type and multi-infarct dementia in accordance with a scored ratio of coherence values, and means for representing such scores.

39. A method of diagnosing a brain condition in a human comprising applying electrodes from an EEG unit about the head of a human, determining a measure of coherence between two brain regions in the head of a subject and wherein the coherence measure is obtained from averaging coherence data from multiple selected electrode pairs located about the head of the human, applying a coherence value as a diagnostic evaluation of the brain condition thereby to facilitate distinguishing between a dementia condition of the Alzheimer's-type and a condition of multi-infarct dementia, and representing such value.

40. A method of diagnosing a brain condition in a human comprising applying electrodes from an EEG unit about the head of a human, determining a measure of coherence between at let two brain regions linked by neuroanatomic tracts in the head of a subject, and wherein the coherence measure is obtained from averaging coherence data from multiple selected electrodes located about the head of a human, applying a coherence value as a diagnostic evaluation of the brain condition, and representing such value.

41. A method as claimed in claim 40 wherein the electrodes are applied as bipolar pairs.

42. A method as claimed in claim 41 wherein the value facilitates distinguishing between conditions with different functional connections related to brain dysfunction of the underlying tracts.

43. A method as claimed in claim 40 wherein the value facilitates distinguishing between conditions with different functional connections related to brain dysfunction of the underlying tracts.

44. A method of diagnosing a brain condition in a human comprising applying electrodes from an EEG unit about the head of a human, determining at least two coherence values of a brain region in the head of the subject, the one coherence value being a coherence value within the posterior cortex, and second coherence value being that between the front and the back of the brain, applying a relationship between the values as a diagnostic evaluation of a brain condition, and presenting such relationship.

* * * * *